United States Patent
Ju et al.

(10) Patent No.: US 8,569,066 B2
(45) Date of Patent: Oct. 29, 2013

(54) GENETICALLY ENGINEERED RECOMBINANT ESCHERICHIA COLI PRODUCING L-TRYPTOPHAN HAVING ORIGINALLY L-PHENYLALANINE PRODUCTIVITY, AND METHOD FOR PRODUCING L-TRYPTOPHAN USING THE MICROORGANISM

(75) Inventors: Jae-yeong Ju, Gyeonggi-do (KR); Hyang Choi, Gyeonggi-do (KR); Eun-sung Koh, Gyeonggi-do (KR); Ji-sun Lee, Incheon (KR); Jin-ho Lee, Gyeonggi-do (KR); So-young Kim, Gyeonggi-do (KR); Chang-hyun Jin, Gyeonggi-do (KR); Young-hoon Park, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 13/548,044

(22) Filed: Jul. 12, 2012

(65) Prior Publication Data

US 2012/0276639 A1    Nov. 1, 2012

Related U.S. Application Data

(62) Division of application No. 12/520,350, filed as application No. PCT/KR2007/006933 on Dec. 28, 2007.

(30) Foreign Application Priority Data

Dec. 29, 2006    (KR) .................. 10-2006-0137650

(51) Int. Cl.
*C12N 15/09*    (2006.01)
*C12N 1/21*    (2006.01)
*C12P 13/22*    (2006.01)

(52) U.S. Cl.
USPC ................. 435/471; 435/108; 435/252.33

(58) Field of Classification Search
None
See application file for complete search history.

(56) References Cited

U.S. PATENT DOCUMENTS

2010/0028956 A1    2/2010    Ju

FOREIGN PATENT DOCUMENTS

| EP | 0488424 | 6/1992 |
|---|---|---|
| EP | 0789073 | 8/2001 |
| GB | 2304718 | 3/1997 |
| KR | 85-0001232 | 8/1985 |
| KR | 87-0001813 | 10/1987 |
| KR | 90-0005772 | 8/1990 |
| KR | 90-0005773 | 8/1990 |
| KR | 90-0008251 | 11/1990 |
| KR | 91-0005672 | 8/1991 |
| KR | 92-0007405 | 8/1992 |
| WO | WO 87/01130 | 2/1987 |
| WO | WO 2005/056776 | 6/2005 |

OTHER PUBLICATIONS

Datsenko and Wanner (2000) Proc. Natl. Acad. Sci. USA 97(12):6640-6645, "One-step inactivation of chromosomal genes in *Escherichia coli* K-12 using PCR products".
European Search Report issued May 31, 2010 in European Patent Application Serial No. 07860723.1.
Kwak et al. (1999) J. Biochem. Mol. Biol. 32(1):20-24, "Identification of Amino Acid Residues Involved in Feedback Inhibition of the Anthranilate Synthase in *Escherichia coli*".
LeBlanc et al. (1992) Plasmid 28(2):130-45 "Molecular, Genetic and Functional Analysis of the Basic Replicon of pVA380-1, A Plasmid of Oral Streptococcal Origin".
Ohshima et al. (2002) J. Bacteriol. 184(2):381-389, "Molecular Organization of Intrinsic Restriction and Modification Genes BsuM of *Bacillus subtilis* Marburg".
Pozzi et al. (1996) J. Bacteriol. 178(20):6087-6090, "Competence for Genetic Transformation in Encapsulated Strains of *Streptococcus pneumoniae*: Two Allelic Variants of the Peptide Pheromone".

*Primary Examiner* — Rebecca Prouty
(74) *Attorney, Agent, or Firm* — Swanson & Bratschun, LLC

(57) ABSTRACT

The present invention relates to a microorganism having L-tryptophan productivity and a method for producing L-tryptophan using the same. More precisely, the present invention relates to the recombinant *E. coli* strain CJ600 (KCCM 10812P) having tryptophan productivity produced from the mutant form (KFCC 10066) of *E. coli* having L-phenylalanine productivity, wherein tryptophan auxotrophy is released, L-phenylalanine biosynthesis is blocked but tryptophan productivity is enhanced by reinforcing the gene involved in tryptophan biosynthesis, and a method of producing L-tryptophan using the same.

2 Claims, No Drawings

SEQUENCE LISTING

<160> NUMBER OF SEQ ID NOS: 39

<210> SEQ ID NO 1
<211> LENGTH: 38
<212> TYPE: DNA
<213> ORGANISM: Artificial Sequence
<220> FEATURE:
<223> OTHER INFORMATION: primer 1

<400> SEQUENCE: 1
aggcaacact atgacatcgt gtaggctgga gctgcttc                              38

<210> SEQ ID NO 2
<211> LENGTH: 40
<212> TYPE: DNA
<213> ORGANISM: Artificial Sequence
<220> FEATURE:
<223> OTHER INFORMATION: primer 2

<400> SEQUENCE: 2
ggtcgccatt aacaacgtgg catatgaata tcctccttag                            40

<210> SEQ ID NO 3
<211> LENGTH: 19
<212> TYPE: DNA
<213> ORGANISM: Artificial Sequence
<220> FEATURE:
<223> OTHER INFORMATION: primer 3

<400> SEQUENCE: 3
tattgagtgt atcgccaac                                                   19

<210> SEQ ID NO 4
<211> LENGTH: 18
<212> TYPE: DNA
<213> ORGANISM: Artificial Sequence
<220> FEATURE:
<223> OTHER INFORMATION: primer 4

<400> SEQUENCE: 4
cgatgtcata gtgttgcc                                                    18

<210> SEQ ID NO 5
<211> LENGTH: 20
<212> TYPE: DNA
<213> ORGANISM: Artificial Sequence

```
<220> FEATURE:
<223> OTHER INFORMATION: primer 5

<400> SEQUENCE: 5
ccacgttgtt aatggcgacc                                                  20

<210> SEQ ID NO 6
<211> LENGTH: 20
<212> TYPE: DNA
<213> ORGANISM: Artificial Sequence
<220> FEATURE:
<223> OTHER INFORMATION: primer 6

<400> SEQUENCE: 6
ttcattgaac gggtgatttc                                                  20

<210> SEQ ID NO 7
<211> LENGTH: 70
<212> TYPE: DNA
<213> ORGANISM: Artificial Sequence
<220> FEATURE:
<223> OTHER INFORMATION: primer 7

<400> SEQUENCE: 7
tccgcacgtt tatgatatgc tatcgtactc tttagcgagt acaaccgggg gtgtaggctg      60
gagctgcttc                                                             70

<210> SEQ ID NO 8
<211> LENGTH: 70
<212> TYPE: DNA
<213> ORGANISM: Artificial Sequence
<220> FEATURE:
<223> OTHER INFORMATION: primer 8

<400> SEQUENCE: 8
gccacgtctt atcaggccta caaaatcaat cgcttttcag caacacctct catatgaata      60
tcctccttag                                                             70

<210> SEQ ID NO 9
<211> LENGTH: 20
<212> TYPE: DNA
<213> ORGANISM: Artificial Sequence
<220> FEATURE:
<223> OTHER INFORMATION: primer 9

<400> SEQUENCE: 9
gcgccgggcg tatcgacgca                                                  20

<210> SEQ ID NO 10
<211> LENGTH: 20
<212> TYPE: DNA
<213> ORGANISM: Artificial Sequence
<220> FEATURE:
<223> OTHER INFORMATION: primer 10

<400> SEQUENCE: 10
gcatatcata aacgtgcgga                                                  20

<210> SEQ ID NO 11
<211> LENGTH: 20
<212> TYPE: DNA
<213> ORGANISM: Artificial Sequence
<220> FEATURE:
<223> OTHER INFORMATION: primer 11

<400> SEQUENCE: 11
```
tgtaggcctg ataagacgtg                                              20

<210> SEQ ID NO 12
<211> LENGTH: 20
<212> TYPE: DNA
<213> ORGANISM: Artificial Sequence
<220> FEATURE:
<223> OTHER INFORMATION: primer 12

<400> SEQUENCE: 12 aagggcgat cggcgtgttt                                               20

<210> SEQ ID NO 13
<211> LENGTH: 70
<212> TYPE: DNA
<213> ORGANISM: Artificial Sequence
<220> FEATURE:
<223> OTHER INFORMATION: primer 13

<400> SEQUENCE: 13
atggcaacac taaccaccac ccaaacgtca ccgtcgctgc ttggcggcgt gtgtaggctg   60
gagctgcttc                                                         70

<210> SEQ ID NO 14
<211> LENGTH: 70
<212> TYPE: DNA
<213> ORGANISM: Artificial Sequence
<220> FEATURE:
<223> OTHER INFORMATION: primer 14

<400> SEQUENCE: 14
ttactgatac accggcagta aattaaagct cgataaaata tgcaccagtg catatgaata   60
tcctccttag                                                         70

<210> SEQ ID NO 15
<211> LENGTH: 20
<212> TYPE: DNA
<213> ORGANISM: Artificial Sequence
<220> FEATURE:
<223> OTHER INFORMATION: primer 15

<400> SEQUENCE: 15
gcagccgtta cattggtaac                                              20

<210> SEQ ID NO 16
<211> LENGTH: 20
<212> TYPE: DNA
<213> ORGANISM: Artificial Sequence
<220> FEATURE:
<223> OTHER INFORMATION: primer 16

<400> SEQUENCE: 16
gtggtggtta gtgttgccat                                              20

<210> SEQ ID NO 17
<211> LENGTH: 20
<212> TYPE: DNA
<213> ORGANISM: Artificial Sequence
<220> FEATURE:
<223> OTHER INFORMATION: primer 17

<400> SEQUENCE: 17
tactgccggt gtatcagtaa                                              20

-continued

```
<210> SEQ ID NO 18
<211> LENGTH: 20
<212> TYPE: DNA
<213> ORGANISM: Artificial Sequence
<220> FEATURE:
<223> OTHER INFORMATION: primer 18

<400> SEQUENCE: 18
tcaaaccgtc agcacggctg                                                    20

<210> SEQ ID NO 19
<211> LENGTH: 70
<212> TYPE: DNA
<213> ORGANISM: Artificial Sequence
<220> FEATURE:
<223> OTHER INFORMATION: primer 19

<400> SEQUENCE: 19
atgaaggatt atgtaatgga aaactttaaa catctccctg aaccgttccg gtgtaggctg        60
gagctgcttc                                                               70

<210> SEQ ID NO 20
<211> LENGTH: 70
<212> TYPE: DNA
<213> ORGANISM: Artificial Sequence
<220> FEATURE:
<223> OTHER INFORMATION: primer 20

<400> SEQUENCE: 20
ttagccaaat ttaggtaaca cgttaaagac gttgccgaac cagcacaaaa catatgaata       60
tcctccttag                                                               70

<210> SEQ ID NO 21
<211> LENGTH: 21
<212> TYPE: DNA
<213> ORGANISM: Artificial Sequence
<220> FEATURE:
<223> OTHER INFORMATION: primer 21

<400> SEQUENCE: 21
ttaagcgaaa tcaccgggga a                                                  21

<210> SEQ ID NO 22
<211> LENGTH: 18
<212> TYPE: DNA
<213> ORGANISM: Artificial Sequence
<220> FEATURE:
<223> OTHER INFORMATION: primer 22

<400> SEQUENCE: 22
atgtccgagc actggcgc                                                      18

<210> SEQ ID NO 23
<211> LENGTH: 33
<212> TYPE: DNA
<213> ORGANISM: Artificial Sequence
<220> FEATURE:
<223> OTHER INFORMATION: primer 23

<400> SEQUENCE: 23
tgctctagag atcctttta acccatcaca tat                                      33

<210> SEQ ID NO 24
<211> LENGTH: 33
<212> TYPE: DNA
<213> ORGANISM: Artificial Sequence
```

```
<220> FEATURE:
<223> OTHER INFORMATION: primer 24

<400> SEQUENCE: 24
cgcggatcct cgtgatggca ggttgggcgt cgc                              33

<210> SEQ ID NO 25
<211> LENGTH: 30
<212> TYPE: DNA
<213> ORGANISM: Artificial Sequence
<220> FEATURE:
<223> OTHER INFORMATION: primer 25

<400> SEQUENCE: 25
cgcggatccg aaaagcgatc cataagatat                                 30

<210> SEQ ID NO 26
<211> LENGTH: 30
<212> TYPE: DNA
<213> ORGANISM: Artificial Sequence
<220> FEATURE:
<223> OTHER INFORMATION: primer 26

<400> SEQUENCE: 26
cgcgtcgact gctggcaggc ctgctttgtt                                 30

<210> SEQ ID NO 27
<211> LENGTH: 30
<212> TYPE: DNA
<213> ORGANISM: Artificial Sequence
<220> FEATURE:
<223> OTHER INFORMATION: primer 27

<400> SEQUENCE: 27
cgatatgatc accctacaat atctcgctga                                 30

<210> SEQ ID NO 28
<211> LENGTH: 30
<212> TYPE: DNA
<213> ORGANISM: Artificial Sequence
<220> FEATURE:
<223> OTHER INFORMATION: primer 28

<400> SEQUENCE: 28
tcagcgagat attgtagggt gatcatatcg                                 30

<210> SEQ ID NO 29
<211> LENGTH: 30
<212> TYPE: DNA
<213> ORGANISM: Artificial Sequence
<220> FEATURE:
<223> OTHER INFORMATION: primer 29

<400> SEQUENCE: 29
cgcggatcca ccgtggaaat ttccacgccg                                 30

<210> SEQ ID NO 30
<211> LENGTH: 30
<212> TYPE: DNA
<213> ORGANISM: Artificial Sequence
<220> FEATURE:
<223> OTHER INFORMATION: primer 30

<400> SEQUENCE: 30
cgcgtcgact ttccgctgac agttgcggta                                 30
```

```
<210> SEQ ID NO 31
<211> LENGTH: 33
<212> TYPE: DNA
<213> ORGANISM: Artificial Sequence
<220> FEATURE:
<223> OTHER INFORMATION: primer 31

<400> SEQUENCE: 31
gcttatcgcg acaatgccac cgcgcttttt cac                              33

<210> SEQ ID NO 32
<211> LENGTH: 33
<212> TYPE: DNA
<213> ORGANISM: Artificial Sequence
<220> FEATURE:
<223> OTHER INFORMATION: primer 32

<400> SEQUENCE: 32
gtgaaaaagc gcggtggcat tgtcgcgata agc                              33

<210> SEQ ID NO 33
<211> LENGTH: 1161
<212> TYPE: DNA
<213> ORGANISM: Escherichia coli

<400> SEQUENCE: 33
atgacatcgg aaaacccgtt actggcgctg cgagagaaaa tcagcgcgct ggatgaaaaa     60
ttattagcgt tactggcaga acggcgcgaa ctggccgtcg aggtgggaaa agccaaactg    120
ctctcgcatc gcccggtacg tgatattgat cgtgaacgcg atttgctgga agattaatt    180 acgctcggta aagcgcacca tctggacgcc cattacatta ctcgcctgtt ccagctcatc    240
attgaagatt ccgtattaac tcagcaggct ttgctccaac aacatctcaa taaaattaat    300
ccgcactcag cacgcatcgc ttttctcggc cccaaaggtt cttattccca tcttgcggcg    360
cgccagtatg ctgcccgtca ctttgagcaa ttcattgaaa gtggctgcgc caaatttgcc    420 gatatttta atcaggtgga aaccggccag ccgactatg ccgtcgtacc gattgaaaat    480
accagctccg gtgccataaa cgacgtttac gatctgctgc aacataccag cttgtcgatt    540
gttggcgaga tgacgttaac tatcgaccat tgtttgttgg tctccggcac tactgattta    600
tccaccatca atacggtcta cagccatccg cagccattcc agcaatgcag caaattcctt    660
aatcgttatc cgcactggaa gattgaatat accgaaagta cgtctgcggc aatggaaaag    720
gttgcacagg caaatcacc gcatgttgct gcgttgggaa gcgaagctgg cggcactttg    780
tacggtttgc aggtactgga gcgtattgaa gcaaatcagc gacaaaactt cacccgattt    840
gtggtgttgg cgcgtaaagc cattaacgtg tctgatcagg ttccggcgaa accacgttg    900 ttaatggcga ccgggcaaca agccggtgcg ctggttgaag cgttgctggt actgcgcaac    960
cacaatctga ttatgacccg tctggaatca cgcccgattc acgtaatcc atggaagag   1020 atgttctatc tggatattca ggccaatctt gaatcagcgg aaatgcaaaa agcattgaaa   1080
gagttagggg aaatcacccg ttcaatgaag gtattgggct gttacccaag tgagaacgta   1140
gtgcctgttg atccaacctg a                                           1161

<210> SEQ ID NO 34
<211> LENGTH: 327
<212> TYPE: DNA
<213> ORGANISM: Escherichia coli

<400> SEQUENCE: 34
atggcccaac aatcacccta ttcagcagcg atggcagaac agcgtcacca ggagtggtta     60
```

-continued

| | |
|---|---|
| cgttttgtcg acctgcttaa gaatgcctac caaaacgatc tccatttacc gttgttaaac | 120 |
| ctgatgctga cgccagatga gcgcgaagcg ttggggactc gcgtgcgtat tgtcgaagag | 180 |
| ctgttgcgcg gcgaaatgag ccagcgtgag ttaaaaaatg aactcggcgc aggcatcgcg | 240 |
| acgattacgc gtggatctaa cagcctgaaa gccgcgcccg tcgagctgcg ccagtggctg | 300 |
| gaagaggtgt tgctgaaaag cgattga | 327 |

<210> SEQ ID NO 35
<211> LENGTH: 1245
<212> TYPE: DNA
<213> ORGANISM: Escherichia coli

<400> SEQUENCE: 35

| | |
|---|---|
| atggcaacac taaccaccac ccaaacgtca ccgtcgctgc ttggcggcgt ggtgattatc | 60 |
| ggcggcacca ttattggcgc agggatgttt tctctgccag tggtcatgtc cggggcgtgg | 120 |
| tttttctggt caatggcggc gctgatcttt acctggttct gtatgctgca ttccggcttg | 180 |
| atgattctgg aagctaacct gaattacaga atcggttcga gttttgacac catcaccaaa | 240 |
| gatttgctgg gcaaaggctg gaacgtggtc aacggcattt ccattgcctt tgtgctctat | 300 |
| atcctgacct atgcctatat ttctgccagt ggttcgattc tgcatcacac cttcgcagag | 360 |
| atgtcactaa acgtcccggc acgggcggcg gttttggtt ttgcattgct ggtagcgttt | 420 |
| gtggtgtggt tgagcactaa agccgtcagt cgcatgacag cgattgtgct gggggcgaaa | 480 |
| gtcattacct tcttcctcac ctttggtagc ctgctgggc atgtgcagcc tgcgacattg | 540 |
| ttcaacgtcg ccgaaagcaa tgcgtcttat gcaccgtatc tgttgatgac cctgccgttc | 600 |
| tgtctggcat cgtttggtta tcacggtaac gtgccaagcc tgatgaagta ttacggcaaa | 660 |
| gatccgaaaa ccatcgtgaa atgtctggtg tacggtacgc tgatggcgct ggcgctgtat | 720 |
| accatctggt tgctggcgac gatgggtaac atcccgcgtc cggagtttat cggtattgca | 780 |
| gagaagggcg gtaatattga tgtgctggta caggcgttaa gcggcgtact gaacagccgt | 840 |
| agtctggatc tgctgctggt cgtgttctca aactttgcgg tagcgagttc gttcctcggc | 900 |
| gtaacgctgg gtttgtttga ctatctggca gatctgtttg gtttcgacga ctcggctgtg | 960 |
| ggccgcttga aaacggcatt gctgaccttt gccccgccag ttgtgggggg gctgttgttc | 1020 |
| ccgaacggat tcctgtacgc cattggttat gctggtttag cggctaccat ctgggcggca | 1080 |
| attgttccgg cgctgttagc ccgtgcatcg cgtaaacgct ttggcagccc gaaattccgc | 1140 |
| gtctggggtg gcaagccgat gattgcgctg attctggtgt ttggcgtcgg caacgcactg | 1200 |
| gtgcatattt tatcgagctt taatttactg ccggtgtatc agtaa | 1245 |

<210> SEQ ID NO 36
<211> LENGTH: 1416
<212> TYPE: DNA
<213> ORGANISM: Escherichia coli

<400> SEQUENCE: 36

| | |
|---|---|
| atggaaaact ttaaacatct ccctgaaccg ttccgcattc gtgttattga gccagtaaaa | 60 |
| cgtaccactc gcgcttatcg tgaagaggca attattaaat ccggtatgaa cccgttcctg | 120 |
| ctggatagca agatgttttt tatcgattta ctgaccgaca cggcaccgg gcggtgacg | 180 |
| cagagcatgc aggctgcgat gatgcgcggc gacgaagcct acagcggcag tcgtagctac | 240 |
| tatgcgttag ccgagtcagt gaaaaatatc tttggttatc aatacaccat tccgactcac | 300 |
| cagggccgtg gcgcagagca atctctatatt ccggtactga ttaaaaaacg cgagcaggaa | 360 |

```
aaaggcctgg atcgcagcaa aatggtggcg ttctctaact atttctttga taccacgcag    420
ggccatagcc agatcaacgg ctgtaccgtg cgtaacgtct atatcaaaga agccttcgat    480
acgggcgtgc gttacgactt taaaggcaac tttgaccttg agggattaga acgcggtatt    540
gaagaagttg gtccgaataa cgtgccgtat atcgttgcaa ccatcaccag taactctgca    600
ggtggtcagc cggttttcact ggcaaactta aaagcgatgt acagcatcgc gaagaaatac    660
gatattccgg tggtaatgga ctccgcgcgc tttgctgaaa acgcctattt catcaagcag    720
cgtgaagcag aatacaaaga ctggaccatc gagcagatca cccgcgaaac ctacaaatat    780
gccgatatgc tggcgatgtc cgccaagaaa gatgcgatgg tgccgatggg cggcctgctg    840
tgcatgaaag acgacagctt ctttgatgtg tacaccgagt gcagaaccct ttgcgtggtg    900
caggaaggct tcccgacata tggcggcctg gaaggcggcg cgatggagcg tctggcggta    960
ggtctgtatg acggcatgaa tctcgactgg ctggcttatc gtatcgcgca ggtacagtat   1020
ctggtcgatg gtctggaaga gattggcgtt gtctgccagc aggcgggcgg tcacgcggca   1080
ttcgttgatg ccggtaaact gttgccgcat atcccggcag accagttccc ggcacaggcg   1140
ctggcctgcg agctgtataa agtcgccggt atccgtgcgg tagaaattgg ctctttcctg   1200
ttaggccgcg atccgaaaac cggtaaacaa ctgccatgcc cggctgaact gctgcgttta   1260
accattccgc gcgcaacata tactcaaaca catatggact tcattattga agcctttaaa   1320
catgtgaaag agaacgcggc gaatattaaa ggattaacct ttacgtacga accgaaagta   1380
ttgcgtcact tcaccgcaaa acttaaagaa gtttaa                              1416

<210> SEQ ID NO 37
<211> LENGTH: 1248
<212> TYPE: DNA
<213> ORGANISM: Escherichia coli

<400> SEQUENCE: 37
atgactgatc aagctgaaaa aaagcactct gcattttggg gtgttatggt tatagcaggt     60
acagtaattg gtggaggtat gtttgcttta cctgttgatc ttgccggtgc ctggtttttc    120
tggggtgcct ttatccttat cattgcctgg ttttcaatgc ttcattccgg ttattgtta    180 ttagaagcaa atttaaatta tcccgtcggc tccagttta acaccatcac caaagattta    240
atcggtaaca cctggaacat tatcagcggt attaccgttg ccttcgttct ctatatcctc    300
acttatgcct atatctctgc taatggtgcg atcattagtg aaacgatatc aatgaatttg    360
ggttatcacg ctaatccacg tattgtcggg atctgcacag ccattttcgt tgccagcgta    420
ttgtggttaa gttcgttagc cgccagtcgt attacctcat tgttcctcgg gctgaagatt    480
atctcctttg tgatcgtgtt tggttctttt tcttccagg tcgattactc cattctgcgc    540
gacgccacca gctccactgc gggaacgtct tacttcccgt atatctttat ggctttgccg    600
gtgtgtctgg cgtcatttgg tttccacggc aatattccca gcctgattat ttgctatgga    660
aaacgcaaag ataagttaat caaaagcgtg gtatttggtt cgctgctggc gctggtgatt    720
tatctcttct ggctctattg caccatgggg aatattccgc gagaaagctt taaggcgatt    780
atctcctcag gcggcaacgt tgattcgctg gtgaaatcgt tcctcggcac caaacagcac    840
ggcattatcg agttttgcct gctggtgttc tctaacttag ctgttgccag ttcgttcttt    900
ggtgtcacgc tggggttgtt cgattatctg gcggacctgt ttaagattga taactcccac    960
ggcgggcgtt tcaaaaccgt gctgttaacc ttcctgccac ctgcgttgtt gtatctgatc   1020
ttcccgaacg gctttatttta cgggatcggc ggtgccgggc tgtgcgccac catctgggcg   1080
```

```
gtcattattc cgcagtgct tgcaatcaaa gctcgcaaga agtttcccaa tcagatgttc    1140
acggtctggg gcggcaatct tattccggcg attgtcattc tctttggtat aaccgtgatt    1200
ttgtgctggt tcggcaacgt ctttaacgtg ttacctaaat ttggctaa                 1248
```

<210> SEQ ID NO 38
<211> LENGTH: 1053
<212> TYPE: DNA
<213> ORGANISM: Escherichia coli
<220> FEATURE:
<221> NAME/KEY: mutation
<222> LOCATION: (449)
<223> OTHER INFORMATION: 449 nucleotide c -> t mutation, P150L

<400> SEQUENCE: 38

```
atgaattatc agaacgacga tttacgcatc aaagaaatca agagttact tcctcctgtc      60 gcattgctgg aaaaattccc cgctactgaa aatgccgcga atacggttgc ccatgcccga    120
aaagcgatcc ataagatcct gaaaggtaat gatgatcgcc tgttggttgt gattggccca    180
tgctcaattc atgatcctgt cgcggcaaaa gagtatgcca ctcgcttgct ggcgctgcgt    240
gaagagctga aagatgagct ggaaatcgta atgcgcgtct attttgaaaa gccgcgtacc    300
acggtgggct ggaaagggct gattaacgat ccgcatatgg ataatagctt ccagatcaac    360
gacggtctgc gtatagcccg taaattgctg cttgatatta cgacagcgg tctgccagcg    420 gcaggtgagt ttctcgatat gatcacccta caatatctcg ctgacctgat gagctggggc    480
gcaattggcg cacgtaccac cgaatcgcag gtgcaccgcg aactggcatc agggctttct    540
tgtccggtcg gcttcaaaaa tggcaccgac ggtacgatta agtggctat cgatgccatt    600 aatgccgccg gtgcgccgca ctgcttcctg tccgtaacga aatgggggca ttcggcgatt    660
gtgaatacca gcggtaacgg cgattgccat atcattctgc gcggcggtaa agagcctaac    720
tacagcgcga agcacgttgc tgaagtgaaa gaagggctga acaaagcagg cctgccagca    780
caggtgatga tcgatttcag ccatgctaac tcgtccaaac aattcaaaaa gcagatggat    840
gtttgtgctg acgtttgcca gcagattgcc ggtggcgaaa aggccattat ggcgtgatg    900 gtggaaagcc atctggtgga aggcaatcag agcctcgaga gcggggagcc gctggcctac    960
ggtaagagca tcaccgatgc ctgcatcggc tgggaagata ccgatgctct gttacgtcaa   1020
ctggcgaatg cagtaaaagc gcgtcgcggg taa                                1053
```

<210> SEQ ID NO 39
<211> LENGTH: 1563
<212> TYPE: DNA
<213> ORGANISM: Escherichia coli
<220> FEATURE:
<221> NAME/KEY: mutation
<222> LOCATION: (61)
<223> OTHER INFORMATION: c -> t mutation, P21S

<400> SEQUENCE: 39

```
atgcaaacac aaaaaccgac tctcgaactg ctaacctgcg aaggcgctta tcgcgacaat      60
tccaccgcgc tttttcacca gttgtgtggg gatcgtccgg caacgctgct gctggaatcc    120
gcagatatcg acagcaaaga tgatttaaaa agcctgctgc tggtagacag tgcgctgcgc    180
attacagctt taggtgacac tgtcacaatc caggcacttt ccggcaacgg cgaagccctc    240
ctggcactac tggataacgc cctgcctgcg ggtgtggaaa gtgaacaatc accaaactgc    300
cgtgtgctgc gcttcccccc tgtcagtcca ctgctggatg aagacgcccg cttatgctcc    360
ctttcggttt tgacgctttt ccgtttattg cagaatctgt tgaatgtacc gaaggaagaa    420
```

```
cgagaagcca tgttcttcgg cggcctgttc tcttatgacc ttgtggcggg atttgaagat      480
ttaccgcaac tgtcagcgga aaataactgc cctgatttct gtttttatct cgctgaaacg      540
ctgatggtga ttgaccatca gaaaaaaagc acccgtattc aggccagcct gtttgctccg      600
aatgaagaag aaaaacaacg tctcactgct cgcctgaacg aactacgtca gcaactgacc      660
gaagccgcgc cgccgctgcc agtggtttcc gtgccgcata tgcgttgtga atgtaatcag      720
agcgatgaag agttcggtgg cgtagtgcgt ttgttgcaaa aagcgattcg cgctggagaa      780
attttccagg tggtgccatc tcgccgtttc tctctgccct gcccgtcacc gctggcggcc      840
tattacgtgc tgaaaaagag taatcccagc ccgtacatgt tttttatgca ggataatgat      900
ttcaccctat ttggcgcgtc gccggaaagc tcgctcaagt atgatgccac cagccgccag      960
attgagatct acccgattgc cggaacacgc ccacgcggtc gtcgcgccga tggttcactg     1020
gacagagatc tcgacagccg tattgaactg gaaatgcgta ccgatcataa agagctgtct     1080
gaacatctga tgctggttga tctcgcccgt aatgatctgg cacgcatttg caccccccggc     1140 agccgctacg tcgccgatct caccaaagtt gaccgttatt cctatgtgat gcacctcgtc     1200
tctcgcgtag tcggcgaact gcgtcacgat cttgacgccc tgcacgctta tcgcgcctgt     1260
atgaatatgg ggacgttaag cggtgcgccg aaagtacgcg ctatgcagtt aattgccgag     1320
gcggaaggtc gtcgccgcgg cagctacggc ggcgcggtag gttatttcac cgcgcatggc     1380
gatctcgaca cctgcattgt gatccgctcg gcgctggtgg aaaacggtat cgccaccgtg     1440
caagcgggtg ctggtgtagt ccttgattct gttccgcagt cggaagccga cgaaacccgt     1500
aacaaagccc gcgctgtact gcgcgctatt gccaccgcgc atcatgcaca ggagactttc     1560
tga                                                                    1563
```

GENETICALLY ENGINEERED RECOMBINANT *ESCHERICHIA COLI* PRODUCING L-TRYPTOPHAN HAVING ORIGINALLY L-PHENYLALANINE PRODUCTIVITY, AND METHOD FOR PRODUCING L-TRYPTOPHAN USING THE MICROORGANISM

RELATED APPLICATIONS

This application is a divisional application of U.S. patent application Ser. No. 12/520,350, filed Jun. 19, 2009, entitled "Genetically Engineered Recombinant *Escherichia Coli* Producing L-Tryptophan Having Originally L-Phenylalanine Productivity, and Method for Producing L-Tryptophan Using the Microorganism," which is a 35 U.S.C. §371 national phase application of PCT/KR2007/006933 (WO 2008/082179), filed on Dec. 28, 2007, entitled "Genetically Engineered Recombinant *Escherichia Coli* Producing L-Tryptophan Having Originally L-Phenylalanine Productivity, and Method for Producing L-Tryptophan Using the Microorganism," which application claims the benefit of Korean Patent Application Serial No. 10-2006-0137650, filed on Dec. 29, 2006. Each of these applications is specifically incorporated herein by reference in its entirety.

Incorporated by reference herein in its entirety is the Sequence Listing entitled "sequence_listing.txt", created Jun. 19, 2009, size of 19 kilobytes.

TECHNICAL FIELD

The present invention relates to a microorganism having L-tryptophan productivity and a method for producing L-tryptophan using the same. More particularly, the present invention relates to a recombinant *E. coli* having tryptophan productivity produced by genetic engineering through loss of their tryptophan auxotrophy, blocking of L-phenylalanine biosynthesis and enhancing of gene involved in tryptophan biosynthesis from the mutant *E. coli* KFCC 10066 having L-phenylalanine productivity, and a method for producing L-tryptophan using the same.

BACKGROUND ART

L-tryptophan is one of essential amino acids, which has been used as a feed additive or a raw material for medicines including injections and health foods owing to its hypnotic effect or tranquilizing effect. L-tryptophan has been produced by chemical synthesis, enzyme reaction and microorganism fermentation.

For chemical synthesis, high temperature and high pressure reaction is required and both D type and L type are included in the reaction product, which makes the purification process difficult. Enzyme reaction has problems of high price of indole and serine used as substrates and of instability of the enzyme, as shown in the patent description of Mitsui Toatsu (Korean Patent Publication No. 90-005773).

Therefore, L-tryptophan production has largely depended on direct fermentation using a microorganism. The production of L-tryptophan according to the conventional microorganism fermentation has been mostly carried out in auxotroph and mutant with control-region mutation of various microorganisms including *E. coli* and *Corynebacterium*. With the astonishing advancement of recombinant DNA techniques since 1980, metabolism pathway and its regulation mechanism have been disclosed. Since then, researchers have succeeded in the development of excellent recombinant strains using gene manipulation techniques, which brought remarkable increase in production.

Some of Korean Patents in relation to the production of tryptophan by direct fermentation using a microorganism describe respectively the production of tryptophan by using mutant strains having tryptophan analog resistance or auxotrophy (Korean Patent Publication Nos. 87-1813, 90-8251 and 92-7405) and the production of tryptophan by using recombinant strains (Korean Patent Publication Nos. 90-5772 and 91-5672). In the case of using a tryptophan analog resistant strain, it was a major object to overcome feed-back inhibition of enzymes in tryptophan biosynthesis. In the case of using a recombinant strain, cloning of genes involved in the tryptophan biosynthesis was a major object. And, the above methods scored a great success in fact. However, even though the conventional method for producing L-tryptophan using the conventional mutant *E. coli* has an advantage of L-tryptophan production through usage of inexpensive culture medium, it has a disadvantage of low L-tryptophan productivity. The present inventors considered that the production of L-tryptophan by fermentation of *E. coli* CJ285 (KCCM-10534, PCT/KR2004/003030) which was developed and retained by the company of the present inventors also has a problem of low productivity. Thus, the present inventors considered that the development of excellent mutant strain as a mother strain was important to maximize L-tryptophan productivity by recombinant DNA techniques.

On the other hand, the strain producing L-phenylalanine (KFCC 10066, Korean Patent Publication No. 1985-0001232) had been developed and retained by the company of the present inventors since aromatic amino acid (L-tryptophan, L-phenylalanine and L-tyrosine) can be synthesized on common metabolism pathway. So, the present inventors considered that the proper manipulation of the above strain by genetic engineering techniques could increase L-tryptophan productivity. The present inventors, therefore, used the strain producing L-phenylalanine (KFCC 10066, Korean Patent Publication No. 1985-0001232) as a mother strain for a recombinant *E. coli* strain producing L-tryptophan with high yield through loss of tryptophan auxotrophy, blocking of L-phenylalanine biosynthesis and enhancing of gene involved in tryptophan biosynthesis.

DISCLOSURE OF THE INVENTION

The present invention is provided a tryptophan producing strain developed from the mother *E. coli* strain (KFCC 10066) producing L-phenylalanine by inactivating pheA, trpR, mtr, and tnaAB genes on chromosome and by mutating aroG and trpE genes on chromosome in order to release tryptophan auxotrophy, block L-phenylalanine biosynthesis but induce tryptophan production.

It is another object of the present invention to provide a method for producing L-tryptophan at high concentration by culturing the above recombinant *E. coli* strain in fermentation medium containing glucose by direct fermentation.

The above objects and other objects of the present invention can be achieved by the following embodiments of the present invention.

The present invention is described in detail hereinafter.

BEST MODE

The method for producing L-tryptophan of the present invention comprises the following steps: releasing tryptophan auxotrophy of mutant *E. coli* strain (KFCC 10066) having L-phenylalanine productivity on chromosome; blocking L-phenylalanine biosynthesis, that is inactivating pheA gene involved in L-phenylalanine biosynthesis, trpR gene involved in the regulation of tryptophan biosynthesis, mtr gene involved in intracellular re-entry of the produced tryptophan, and tnaAB gene involved in degradation of the produced tryptophan; enhancing the gene involved in tryptophan biosynthesis, that is mutating aroG gene encoding the enzyme for 3-deoxyarabinose-heptulosonate-7-phosphate (DAHP) synthesis on chromosome and trpE involved in tryptophan biosynthesis for releasing feedback inhibition; and confirming the production of L-tryptophan from the recombinant $E.$ $coli$ strain obtained above in the fermentation medium containing glucose by direct fermentation.

The step of releasing tryptophan auxotrophy includes the method of restoring tryptophan operon gene on the chromosome of a strain producing L-phenylalanine having tryptophan auxotrophy to the form of a wild type strain. The tryptophan operon gene comprises the form of trpEDCBA and is composed of genes required for the conversion of chorismate into tryptophan, suggesting that it is necessary for the strain producing tryptophan. So, the tryptophan operon gene was selected as a target gene to be restored.

The step of blocking L-phenylalanine biosynthesis in this invention includes the method of inactivating genes involved in L-phenylalanine biosynthesis. Herein, "inactivation" indicates the deletion of intracellular active pheA, trpR, mtr, and tnaAB genes or mutation of pheA, trpR, mtr and tnaAB genes so as to reduce the levels of the proteins encoded by those genes.

The pheA gene (NCBI gene ID: 16130520) (SEQ. ID. NO: 33) is the gene encoding the protein necessary for L-phenylalanine biosynthesis in $E. coli$ and competes with tryptophan biosynthesis pathway in chorismate. Therefore, it was selected as a target gene to be inactivated for the production of a strain producing tryptophan.

The trpR gene (NCBI gene ID: 16132210) (SEQ. ID. NO: 34) is the gene encoding the protein TrpR necessary for the regulation of tryptophan operon (trpEDCBA) biosynthesis in $E. coli$, which binds to endogenous tryptophan to be functioning as a repressor by binding the promoter of tryptophan operon. So, inactivation of this protein results in over-expression of tryptophan operon mRNA, indicating the increase of the concentration of tryptophan. Therefore, it was selected as a target gene to be inactivated.

The mtr gene (NCBI gene ID: 16131053) (SEQ. ID. NO: 35) is the gene encoding the protein necessary for the influx of tryptophan from the outside of cells. So, this gene should be deleted from the tryptophan producing strain, which makes the gene as a target to be inactivated.

The tnaAB gene (NCBI gene ID: 90111643, 16131577) (SEQ. ID. NO: 36 and NO: 37) is composed of tnaA encoding the protein necessary for the degradation of intracellular tryptophan and tnaB encoding the protein involved in the influx of extracellular tryptophan. This gene is believed not to be necessary for the culture producing L-tryptophan. So, it was selected as a target gene to be inactivated.

The microorganism of the present invention is prepared by inactivating pheA, trpR, mtr and tnaAB genes existing in chromosome of a microorganism having L-tryptophan productivity. To inactivate those genes, mutation is induced by using a ray such as UV or a chemical. And from the mutants, a strain having inactivated genes encoding pheA, trpR, mtr and tnaAB is selected. The inactivation can be performed by recombinant DNA techniques. For example the inactivation can be achieved by inserting nucleotide sequence or the vector containing the nucleotide sequence having homology with the genes encoding pheA, trpR, mtr and tnaAB into a target microorganism to induce homologous recombination. The nucleotide sequence or vector above can include a dominant selection marker.

In this invention, the inactivated pheA, trpR, mtr and tnaAB genes or their DNA fragments contain polynucleotide sequence having sequence homology with the host pheA, trpR, mtr and tnaAB genes, but theses polynucleotide sequences have such mutation as truncation, deletion, substitution, insertion and inversion so as to be incapable of expressing the proteins encoded by pheA, trpR, mtr and tnaAB genes. The insertion of the inactivated pheA, trpR, mtr and tnaAB genes or their DNA fragments into a host cell can be achieved by transformation, conjugation, transduction or electroporation, but not always limited thereto.

When the inactivated pheA, trpR, mtr and tnaAB genes or their DNA fragments are introduced into a host cell by transformation, the inactivation is induced by mixing the polynucleotide sequences with the strain culture. At this time, the strain can be transformed because it is naturally competent to the insertion of the DNA, but it is preferred to make the strain to be competent for the DNA insertion by proper method in advance (see LeBlanc et al, Plasmid 28, 130-145, 1992; Pozzi et al, J. Bacteriol. 178, 6087-6090, 1996). Through homologous recombination, the wild type chromosome copy of the sequence is inactivated by deletion of a part of pheA, trpR, mtr and tnaAB genes of the genomic DNA or insertion of a foreign DNA fragment.

The step of enhancing the gene involved in tryptophan biosynthesis of the present invention includes the method of mutating the gene involved in tryptophan biosynthesis. Herein, "mutation" indicates that the activity of proteins encoding the aroG and trpE genes is modified to release feedback inhibition.

The aroG (NCBI gene ID: 16128722) (SEQ. ID. NO: 38) is the gene encoding the protein necessary for the synthesis of 7P-2-dehydro-3-deoxy-D-arabinoheptose that is the start point of aromatic amino acid (tryptophan, L-phenylalanine, tyrosine) biosynthesis pathway. It was considered that this gene is necessarily mutated to increase tryptophan productivity.

The trpE (NCBI gene ID: 16129225) (SEQ. ID. NO: 39) is the gene encoding the protein involved in the synthesis of anthranilate. Among genes constituting tryptophan operon, this gene is inhibited by tryptophan. So, it was considered that this gene was necessarily mutated to prevent the inhibition.

The present invention also provides a method for producing L-tryptophan at high concentration with high yield by culturing the recombinant $E. coli$ strain prepared above in fermentation medium containing glucose by direct fermentation.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Construction of a Strain Which Have Lost the Property of Tryptophan Auxotrophy

In this example, tryptophan operon gene existing in the chromosome of the tryptophan auxotrophic strain producing L-phenylalanine was restored to the wild type.

To do so, cell lysate of the wild type *E. coli* infected with P1 phage was used. Precisely, one platinum loop of *E. coli* was inoculated into LB liquid medium (Lurina-Bertani, referred as LB hereinafter; bacto trypton 10 g/l, bacto yeast extract 5 g/l, sodium chloride 10 g/l), followed by culture at 37° C. for overnight. The cultured cells were recovered and resuspended in LB-GMC liquid medium (0.2% glucose, 1 mM magnesium sulfate ($MgSO_4$), 0.05 mM calcium chloride ($CaCl_2$)), followed by infection with 2 μl of P1 phage. After culturing at 37° C. for 30 minutes, the culture product was washed twice with 0.1 M Na-citrate to eliminate the remaining P1 phage. The cells were resuspended in 0.1 ml Na-citrate, which were spreaded on M9 solid minimal medium supplemented with 20 mg/l tyrosine. The obtained colony was confirmed to be able to grow in a tryptophan free medium, suggesting that the strains have lost the property of tryptophan auxotrophy. The constructed strain was named "CJ001 ($Trp^+$)".

Example 2

Construction of a Recombinant Strain Producing L-tryptophan with Inactivated pheA Gene In this example, pheA gene of *E. coli* was inactivated by homologous recombination.

To inactivate the pheA gene, one step inactivation, which is a method using lambda Red recombinase developed by Datsenko K A et al (One-step inactivation of chromosomal genes in *Escherichia coli* K-12 using PCR products, Datsenko K A, Wanner B L., Proc Natl Acad Sci USA. 2000 Jun. 6; 97(12): 6640-5), was used. To confirm the insertion into the gene, chloramphenicol resistant gene of pKD3 was used as a marker. Polymerase chain reaction (referred as PCR hereinafter) was performed by using pKD3 as a template with primer 1 and primer 2 shown in Table 1 comprising a part of pheA gene and a part of the sequence of chloramphenicol resistant gene of pKD3, resulting in the amplification of approximately 1100 bp gene fragment [Sambrook et al, Molecular Cloning, a Laboratory Manual (1989), Cold Spring Harbor Laboratories]. The reaction solution used in this example was PCR HL premix kit (BIONEER, Korea). And PCR was performed as follows; denaturation at 94° C. for 30 seconds, annealing at 55° C. for 30 seconds, elongation at 72° C. for 1 minute (30 cycles). The PCR product was electrophoresed on 0.8% agarose gel. The target band was obtained by elution.

TABLE 1

| Primer 1 | 5'- aggcaacactatgacatcgtgtaggctggagctgcttc -3'<br>(SEQ. ID. NO: 1) |
|---|---|
| Primer 2 | 5'- ggtcgccattaacaacgtggcatatgaatatcctccttag -3'<br>(SEQ. ID. NO: 2) |

To obtain 5' DNA fragment of *E. coli* pheA gene, PCR was performed by using the chromosome of wild type *E. coli* W3110 as a template with primers 3 and 4 shown in table 2, resulting in the amplification of approximately 250 bp gene fragment. The reaction solution used herein was PCR HL premix kit and PCR was performed as follows; denaturation at 94° C. for 30 seconds, annealing at 55° C. for 30 seconds, elongation at 72° C. for 20 seconds (30 cycles). The PCR product was electrophoresed on 0.8% agarose gel. The target band was obtained by elution.

TABLE 2

| Primer 3 | 5'- tattgagtgtatcgccaac -3'<br>(SEQ. ID. NO: 3) |
|---|---|
| Primer 4 | 5'- cgatgtcatagtgttgcc -3'<br>(SEQ. ID. NO: 4) |

To obtain 3' DNA fragment of *E. coli* pheA gene, PCR was performed by using the chromosome of wild type *E. coli* W3110 as a template with primers 5 and 6 shown in table 3, resulting in the amplification of approximately 250 bp gene fragment. The reaction solution used herein was PCR HL premix kit and PCR was performed as follows; denaturation at 94° C. for 30 seconds, annealing at 55° C. for 30 seconds, elongation at 72° C. for 20 seconds (30 cycles). The PCR product was electrophoresed on 0.8% agarose gel. The target band was obtained by elution.

TABLE 3

| Primer 5 | 5'- ccacgttgttaatggcgacc -3'<br>(SEQ. ID. NO: 5) |
|---|---|
| Primer 6 | 5'- ttcattgaacgggtgatttc -3'<br>(SEQ. ID. NO: 6) |

Herein, 18 pairs of the nucleotide sequences of primer 1 and primer 4 were complementary, and 20 pairs of the nucleotide sequences of primer 2 and primer 5 were complementary. Thus, the fragment obtained by PCR using primers 1 and 2, the fragment obtained by PCR using primers 3 and 4 and the fragment obtained by PCR using primers 5 and 6 could be linked as one fragment. The PCR products were amplified by PCR five cycles without primers. Primer 3 and primer 6 were added thereto, followed by PCR 25 cycles. As a result, approximately 1600 bp gene fragment was amplified.

*E. coli* CJ001 transformed with pKD46 by the method of Datsenko K A et al was prepared as a competent strain, followed by induction of the 1600 bp sized gene fragment obtained by PCR, the strains were spreaded on the LB solid medium supplemented with 30 mg/L of chloramphenicol. The obtained strain was confirmed to have inactivated pheA by the 1600 bp sized gene fragment obtained by PCR using primer 3 and primer 6. The resultant recombinant strain was named "CJ100 ($Trp^+\Delta pheA$)".

Example 3

Construction of a Recombinant Microorganism Producing L-tryptophan with Inactivated trpR Gene In this example, trpR gene of *E. coli* was inactivated by homologous recombination.

PCR was performed by using pKD3 as a template with primer 7 and primer 8 shown in Table 4 comprising a part of trpR gene and a part of the sequence of chloramphenicol resistant gene of pKD3, resulting in the amplification of approximately 1100 bp gene fragment. The reaction solution used in this example was PCR HL premix kit. And PCR was performed as follows; denaturation at 94° C. for 30 seconds, annealing at 55° C. for 30 seconds, elongation at 72° C. for 1 minute (30 cycles). The PCR product was electrophoresed on 0.8% agarose gel. The target band was obtained by elution.

TABLE 4

Primer 7  5'-tccgcacgtttatgatatgctatcgtactctttagcgagtacaaccgggggtgtaggctggagctgcttc-3'
(SEQ. ID. NO: 7)

Primer 8  5'-gccacgtcttatcaggcctacaaaatcaatcgcttttcagcaacacctctcatatgaatatcctccttag-3'
(SEQ. ID. NO: 8)

To obtain 5' DNA fragment of *E. coli* trpR gene, PCR was performed by using the chromosome of wild type *E. coli* W3110 as a template with primers 9 and 10 shown in Table 5, resulting in the amplification of approximately 250 bp gene fragment. The reaction solution used herein was PCR HL premix kit and PCR was performed as follows; denaturation at 94° C. for 30 seconds, annealing at 55° C. for 30 seconds, elongation at 72° C. for 20 seconds (30 cycles). The PCR product was electrophoresed on 0.8% agarose gel. The target band was obtained by elution.

TABLE 5

Primer 9   5'- gcgccgggcgtatcgacgca -3'
(SEQ. ID. NO: 9)

Primer 10  5'- gcatatcataaacgtgcgga -3'
(SEQ. ID. NO: 10)

To obtain 3' DNA fragment of *E. coli* trpR gene, PCR was performed by using the chromosome of wild type *E. coli* W3110 as a template with primers 11 and 12 shown in Table 6, resulting in the amplification of approximately 250 bp gene fragment. The reaction solution used herein was PCR HL premix kit and PCR was performed as follows; denaturation at 94° C. for 30 seconds, annealing at 55° C. for 30 seconds, elongation at 72° C. for 20 seconds (30 cycles). The PCR product was electrophoresed on 0.8% agarose gel. The target band was obtained by elution.

TABLE 6

Primer 11  5'- tgtaggcctgataagacgtg -3'
(SEQ. ID. NO: 11)

TABLE 6-continued

Primer 12  5'- aaggggcgatcggcgtgttt -3'
(SEQ. ID. NO: 12)

Herein, 20 pairs of the nucleotide sequences of primer 7 and primer 10 were complementary, and 20 pairs of the nucleotide sequences of primer 8 and primer 11 were complementary. Thus, the fragment obtained by PCR using primers 7 and 8, the fragment obtained by PCR using primers 9 and 10 and the fragment obtained by PCR using primers 11 and 12 could be linked as one fragment. The PCR products were amplified by PCR five cycles without primers. Primer 9 and primer 12 were added thereto, followed by PCR 25 cycles. As a result, approximately 1600 bp gene fragment was amplified.

*E. coli* CJ100 transformed with pKD46 by the method of Datsenko K A et al was generated as a competent strain, followed by induction using the 1600 bp sized gene fragment obtained by PCR. The strains were spreaded on LB solid medium containing chloramphenicol.

The obtained strain was confirmed to have inactivated trpR by the 1600 bp sized gene fragment obtained by PCR using primer 9 and primer 12. The resultant recombinant strain was named "CJ200 (Trp$^+$ΔpheAΔtrpR)".

Example 4

Construction of a Recombinant Strain Producing L-tryptophan with Inactivated mtr Gene In this example, mtr gene of *E. coli* was inactivated by homologous recombination.

PCR was performed by using pKD3 as a template with primer 13 and primer 14 shown in Table 7 comprising a part of mtr gene and a part of the sequence of chloramphenicol resistant gene of pKD3, resulting in the amplification of approximately 1100 bp gene fragment. The reaction solution used in this example was PCR HL premix kit. And PCR was performed as follows; denaturation at 94° C. for 30 seconds, annealing at 55° C. for 30 seconds, elongation at 72° C. for 1 minute (30 cycles). The PCR product was electrophoresed on 0.8% agarose gel. The target band was obtained by elution.

TABLE 7

Primer 13 5'-atggcaacactaaccaccacccaaacgtcaccgtcgctgcttggcggcgtgtgtaggctggagctgcttc -3'
(SEQ. ID. NO: 13)

Primer 14 5'-ttactgatacaccggcagtaaattaaagctcgataaaatatgcaccagtgcatatgaatatcctccttag -3'
(SEQ. ID. NO: 14)

To obtain 5' DNA fragment of *E. coli* mtr gene, PCR was performed by using the chromosome of wild type *E. coli* W3110 as a template with primers 15 and 16 shown in Table 8, resulting in the amplification of approximately 500 bp gene fragment. The reaction solution used herein was PCR HL premix kit and PCR was performed as follows; denaturation at 94° C. for 30 seconds, annealing at 55° C. for 30 seconds, elongation at 72° C. for 30 seconds (30 cycles). The PCR product was electrophoresed on 0.8% agarose gel. The target band was obtained by elution.

TABLE 8

| Primer 15 | 5'- gcagccgttacattggtaac -3' (SEQ. ID. NO: 15) |
|---|---|
| Primer 16 | 5'- gtggtggttagtgttgccat -3' (SEQ. ID. NO: 16) |

To obtain 3' DNA fragment of *E. coli* mtr gene, PCR was performed by using the chromosome of wild type *E. coli* W3110 as a template with primers 17 and 18 shown in Table 9, resulting in the amplification of approximately 500 bp gene fragment. The reaction solution used herein was PCR HL premix kit and PCR was performed as follows; denaturation at 94° C. for 30 seconds, annealing at 55° C. for 30 seconds, elongation at 72° C. for 30 seconds (30 cycles). The PCR product was electrophoresed on 0.8% agarose gel. The target band was obtained by elution.

TABLE 9

| Primer 17 | 5'- tactgccggtgtatcagtaa -3' (SEQ. ID. NO: 17) |
|---|---|
| Primer 18 | 5'- tcaaaccgtcagcacggctg -3' (SEQ. ID. NO: 18) |

Herein, 20 pairs of the nucleotide sequences of primer 13 and primer 16 were complementary, and 20 pairs of the nucleotide sequences of primer 14 and primer 17 were complementary. Thus, the fragment obtained by PCR using primers 13 and 14, the fragment obtained by PCR using primers 15 and 16 and the fragment obtained by PCR using primers 17 and 18 could be linked as one fragment. The PCR products were amplified by PCR five cycles without primers. Primer 15 and primer 18 were added thereto, followed by PCR 25 cycles. As a result, approximately 2100 bp gene fragment was amplified.

*E. coli* CJ200 transformed with pKD46 by the method of Datsenko K A et al was prepared as a competent strain, followed by induction using the 2100 bp sized gene fragment obtained by PCR. The strains were spreaded on LB solid medium containing chloramphenicol.

The obtained strain was confirmed to have inactivated mtr by the 2100 bp sized gene fragment obtained by PCR using primer 15 and primer 18. The resultant recombinant strain was named "CJ300 (Trp⁺ΔpheAΔtrpRΔmtr)".

Example 5

Construction of a Recombinant Strain Producing L-tryptophan with Inactivated tnaAB Gene In this example, tnaAB gene of *E. coli* was inactivated by homologous recombination.

PCR was performed by using pKD3 as a template with primer 19 and primer 20 comprising a part of tnaAB gene and a part of the sequence of chloramphenicol resistant gene of pKD3 shown in Table 10, resulting in the amplification of approximately 1100 bp gene fragment. The reaction solution used in this example was PCR HL premix kit. And PCR was performed as follows; denaturation at 94° C. for 30 seconds, annealing at 55° C. for 30 seconds, elongation at 72° C. for 1 minute (30 cycles). The PCR product was electrophoresed on 0.8% agarose gel. The target band was obtained by elution.

TABLE 10

| Primer 19 | 5'-atgaaggattatgtaatggaaaactttaaacatctccctgaaccgttccggtgtaggctg gagctgcttc-3' (SEQ. ID. NO: 19) |
|---|---|
| Primer 20 | 5'-ttagccaaatttaggtaacacgttaaagacgttgccgaaccagcacaaaacatatga atatcctccttag -3' (SEQ. ID. NO: 20) |

*E. coli* CJ300 transformed with pKD46 by the method of Datsenko K A et al was prepared as a competent strain, followed by induction using the 1100 bp sized gene fragment obtained by PCR. The strains were spreaded on LB solid medium containing chloramphenicol. The strain was confirmed to have inactivated tnaAB by the 1900 bp sized gene fragment obtained by PCR using primer 21 and primer 22. The resultant recombinant strain was named "CJ400 (Trp⁺ΔpheAΔtrpRΔmtrΔtnaAB)".

TABLE 11

| Primer 21 | 5'- ttaagcgaaatcaccggggaa -3' (SEQ. ID. NO: 21) |
|---|---|
| Primer 22 | 5'- atgtccgagcactggcgc -3' (SEQ. ID. NO: 22) |

Example 6

Construction of pSKH Vector Inducing Specific Gene Mutation

In this example, the vector that is able to induce specific gene mutation on chromosome of *E. coli* was constructed.

To do so, sacB gene of *Bacillus subtilis* was inserted into pKCG119 vector used in Korean Patent Publication No. 10-2006-0079297. To select the strains mutated without the insertion of a foreign gene, sacB gene was used.

The sacB gene (1.9 kb) was amplified by PCR using the chromosome of wild type *Bacillus subtilis* (Marburg 168) as a template with primers 23 and 24 (Molecular organization of intrinsic restriction and modification genes BsuM of *Bacillus subtilis* Marburg, Ohshima H, Matsuoka S, Asai K, Sadaie Y.

J Bacteriol. 2002 January; 184(2):381-9). The reaction solution used in this example was PCR HL premix kit. And PCR was performed as follows; denaturation at 94° C. for 30 seconds, annealing at 55° C. for 30 seconds, elongation at 72° C. for 2 minutes (30 cycles).

TABLE 12

| Primer 23 | 5'- tgctctagagatcctttttaacccatcacatat -3' (SEQ. ID. NO: 23) |
|---|---|
| Primer 24 | 5'- cgcggatcctcgtgatggcaggttgggcgtcgc -3' (SEQ. ID. NO: 24) |

The PCR product was digested with Xba I and BamH I, which proceeded to 0.8% agarose gel. As a result, 1.9 kb sized DNA fragment was obtained. The obtained fragment was ligated to pKCG119 vector digested with Xba I and BamH (NEB Ligation kit). E. coli Top10 was transformed with the ligation mixture. The transformed cells were spreaded on LB solid medium containing kanamycin (50 mg/L) and cultured at 37° C. for overnight.

The colony was obtained by toothpick, which was inoculated in 3 mL of LB liquid medium containing kanamycin and cultured for overnight. Plasmid DNA was recovered by using plasmid miniprep kit. Nucleotide sequence of the inserted sacB was identified by DNA sequencing. The constructed vector was named "pSKH".

Example 7

Construction of a Recombinant Strain Producing L-tryptophan with Mutated aroG Gene In this example, aroG gene of E. coli was mutated.
Chromosomal DNA was extracted from a strain producing tryptophan by using Genomic-tip system (QIAGEN). PCR was performed using the chromosomal DNA as a template with primers 25 and 26 shown in Table 13, resulting in the amplification of 660 bp DNA fragment containing ORF of aroG gene. The reaction solution used in this example was PCR HL premix kit. And PCR was performed as follows; denaturation at 94° C. for 30 seconds, annealing at 55° C. for 30 seconds, elongation at 72° C. for 30 seconds (30 cycles). The PCR product was electrophoresed on 0.8% agarose gel. The target band was obtained by elution.

TABLE 13

| Primer 25 | 5'- cgcggatccgaaaagcgatccataagatat -3' (SEQ. ID. NO: 25) |
|---|---|
| Primer 26 | 5'- cgcgtcgactgctggcaggcctgctttgtt -3' (SEQ. ID. NO: 26) |

The aroG gene fragment obtained by the above PCR was ligated to pCR2.1-TOPO vector by using TA cloning kit (Invitrogen). E. coli Top10 was transformed with the ligation mixture. The transformed cells were spreaded on LB solid medium containing ampicillin (100 mg/L) and cultured at 37° C. for overnight. The constructed vector was named "TOPO2.1-aroG".

The colony was obtained by toothpick, which was inoculated in 3 mL of LB liquid medium containing ampicillin and cultured for overnight. Plasmid DNA was recovered by using plasmid miniprep kit (QIAGEN) and the size of TOPO2.1-aroG was measured. To generate mutant form of aroG gene, site directed mutation was performed (QuikChange Site-Directed Mutagenesis Kit, STRATAGENE) using TOPO2.1-aroG vector as a template with primers 27 and 28 shown in Table 14. The reaction conditions were as follows; denaturation at 95° C. for 30 seconds, annealing at 55° C. for 1 minute, and elongation at 68° C. for 6 min 30 seconds (18 cycles). E. coli TOP10 cells were transformed with 12 μL of each reaction solution, which were spreaded on LB solid medium containing ampicillin, followed by culture at 37° C. for overnight. The constructed vector was named "TOPO2.1-maroG".

TABLE 14

| Primer 27 | 5'-cgatatgatcaccctacaatatctcgctga -3' (SEQ. ID. NO: 27) |
|---|---|
| Primer 28 | 5'-tcagcgagatattgtagggtgatcatatcg-3' (SEQ. ID. NO: 28) |

The colony was obtained by toothpick, which was inoculated in 3 mL of LB liquid medium containing ampicillin and cultured for overnight. Plasmid DNA was recovered by using plasmid miniprep kit. Nucleotide sequence of the mutated aroG gene was identified by DNA sequencing. TOPO2.1-maroG containing mutated aroG gene was digested with BamH I and Sal I, which proceeded to 0.8% agarose gel. As a result, 660 bp sized DNA fragment was obtained. The obtained fragment was ligated to pSKH vector digested with BamH I and Sal I. E. coli Top10 cells were transformed with the ligation mixture. The transformed cells were spreaded on LB solid medium containing kanamycin and cultured at 37° C. for overnight. The constructed vector was named "pSKH-maroG".

The colony was obtained by toothpick, which was inoculated in 3 mL of LB liquid medium containing kanamycin and cultured for overnight. Plasmid DNA was recovered by using plasmid miniprep kit (QIAGEN) and the size of pSKH-maroG was measured. The origin of replication of the plasmid was eliminated by digesting with NheI and then ligated. The DNA fragment was introduced into CJ400 which was prepared as a competent cell. The CJ400 was spreaded on LB solid medium containing kanamycin at 37° C. for overnight. PCR was performed using the generated colony with primers 25 and 26, and as a result 4.4 kb band was confirmed. From the result, it was confirmed that pSKH vector containing the mutated aroG gene was successfully introduced into the chromosomal DNA. To eliminate the vector except the part of mutated aroG gene from the chromosomal DNA, the strain was cultured in LB+10% sucrose medium for 16 hours, and spreaded on LB plate medium. The generated colonies were cultured on the solid medium containing kanamycin and on the kanamycin free solid medium. The colonies growing on the antibiotic free medium were selected, followed by DNA sequencing. Then, the mutant strain with a substitution of the $150^{th}$ amino acid of the protein product of the aroG gene with leucine was finally selected. The mutant strain was named "CJ500 (Trp$^+$ΔpheA ΔtrpRΔmtrΔtnaAB aroG$^m$)".

Example 8

Construction of a Recombinant Strain Producing L-tryptophan with Mutated trpE Gene In this example, trpE gene of E. coli was mutated.
Chromosomal DNA was extracted from a strain producing tryptophan by using Genomic-tip system (QIAGEN). PCR was performed using the chromosomal DNA as a template with primers 29 and 30 shown in Table 15, resulting in the amplification of 600 bp DNA fragment containing a part of ORF of trpE gene. The reaction solution used in this example was PCR HL premix kit. And PCR was performed as follows; denaturation at 94° C. for 30 seconds, annealing at 55° C. for 30 seconds, elongation at 72° C. for 30 seconds (30 cycles). The PCR product was electrophoresed on 0.8% agarose gel. The target band was obtained by elution.

TABLE 15

| Primer 29 | 5'- cgcggatccaccgtggaaatttccacgccg -3' (SEQ. ID. NO: 29) |
| Primer 30 | 5'- cgcgtcgactttccgctgacagttgcggta -3' (SEQ. ID. NO: 30) |

The trpE gene fragment obtained by the above PCR was ligated to pCR2.1-TOPO vector by using TA cloning kit (Invitrogen). *E. coli* Top10 was transformed with the ligation mixture. The transformed cells were spreaded on LB solid medium containing ampicillin and cultured at 37° C. for overnight. The constructed vector was named "TOPO2.1-trpE".

The colony was obtained by toothpick, which was inoculated in 3 mL of LB liquid medium containing ampicillin and cultured for overnight. Plasmid DNA was recovered by using plasmid miniprep kit (QIAGEN) and the size of TOPO2.1-trpE was measured. To generate mutant form of trpE gene, site directed mutation was performed using TOPO2.1-trpE vector as a template with primers 31 and 32 shown in Table 16. The reaction conditions were as follows; denaturation at 95° C. for 30 seconds, annealing at 55° C. for 1 minute, and elongation at 68° C. for 6 minutes 30 seconds (18 cycles). *E. coli* TOP10 cells were transformed with 12 μL of each reaction solution, which were spreaded on LB solid medium containing ampicillin, followed by culture at 37° C. for overnight. The constructed vector was named "TOPO2.1-mtrpE".

TABLE 16

| Primer 31 | 5'- gcttatcgcgacaatgccaccgcgcttttcac -3' (SEQ. ID. NO: 31) |
| Primer 32 | 5'- gtgaaaaagcgcggtggcattgtcgcgataagc-3' (SEQ. ID. NO: 32) |

The colony was obtained by toothpick, which was inoculated in 3 mL of LB liquid medium containing ampicillin and cultured for overnight. Plasmid DNA was recovered by using plasmid miniprep kit. Nucleotide sequence of the mutated trpE was identified by DNA sequencing. TOPO2.1-mtrpE plasmid containing mutated trpE gene was digested with BamH I and Sal I, which proceeded to 0.8% agarose gel. As a result, 660 bp sized DNA fragment was obtained. The obtained fragment was ligated to pSKH vector digested with BamH I and Sal I. *E. coli* Top10 cells were transformed with the ligation mixture. The transformed cells were spreaded on LB solid medium containing kanamycin and cultured at 37° C. for overnight. The constructed vector was named "pSKH-mtrpE".

The colony was obtained by toothpick, which was inoculated in 3 mL of LB liquid medium containing kanamycin and cultured for overnight. Plasmid DNA was recovered by using plasmid miniprep kit (QIAGEN) and the size of pSKH-mtrpE was measured. The origin of replication of the plasmid was eliminated by digesting with NheI and then ligated. The DNA fragment was introduced into CJ500, which was spreaded on LB solid medium containing kanamycin at 37° C. for overnight. PCR was performed using the generated colony with primers 29 and 30 and as a result 4.4 kb band was confirmed. From the result, it was confirmed that pSKH vector containing the mutated trpE gene was successfully introduced into the chromosomal DNA. To eliminate the vector except the part of mutated trpE gene from the chromosomal DNA, the strain was cultured in LB+10% sucrose medium for 16 hours, followed by distribution on LB plate medium. The generated colonies were cultured on the solid medium containing kanamycin and on the kanamycin free solid medium. The colonies growing on the antibiotic free medium were selected, followed by DNA sequencing. Then, the mutant strain with a substitution of the 21$^{st}$ amino acid of the protein product of the trpE gene with serine was finally selected. The mutant strain was named "CJ600 (Trp$^+$ΔpheAΔtrpRΔmtrΔtnaAB aroG$^m$ trpE$^m$)", and deposited at KCCM (Korean Culture Center of Microorganisms) of KFCC (Korean Federation of Culture Collection), the International Depository Authority located at 361-221, Hongje-1-Dong, Seodaemungu-Gu, Seoul, Korea, on Dec. 8, 2006 (Accession No: KCCM 10812P).

Example 9

Comparison of Tryptophan Productivity of the Microorganism Constructed by Genetic Recombination In this example, the colonies of the recombinant strains constructed in Example 1-Example 6, CJ001, CJ100, CJ200, CJ300, CJ400, CJ500 and CJ600 (KCCM 10812P) were spreaded on LB solid medium by one platinum loop each, and cultured for overnight. The growing strains were inoculated in flask titer medium having the composition as shown in Table 17 by one platinum loop each. After inoculation, the strains were cultured at 37° C., 200 rpm for 48 hours. The levels of tryptophan and L-phenylalanine obtained from the above culture and the levels of tryptophan and L-phenylalanine obtained from the culture of the mutant *E. coli* KFCC 10066 producing L-phenylalanine were compared. Optical density (OD), and L-tryptophan and L-phenylalanine levels were represented by mean value obtained from three flasks.

TABLE 17

| Composition | Concentration (g/L) |
| --- | --- |
| glucose | 60 |
| yeast extract | 2.5 |
| (NH$_4$)$_2$SO$_4$·7H$_2$O | 20 |
| MgSO$_4$ | 1 |
| Na-citrate | 5 |
| NaCl | 1 |
| L-tyrosine | 0.1 |
| L-phenylalanine | 0.15 |
| CaCO$_3$ | 40 |
| KH$_2$PO$_4$ | 2 |

As a result, as shown in Table 18, L-tryptophan was not produced in the *E. coli* mutant KFCC 10066 producing L-phenylalanine, while 6.5 g/L of L-tryptophan was produced in *E. coli* CJ600 (KCCM 10812P) developed in the present invention.

TABLE 18

| Strain name | Cell OD (562 nm) | L-tryptophan (g/L) | L-phenylalanine (g/l) |
|---|---|---|---|
| KFCC 10066 | 15.2 | 0.0 | 9.1 |
| CJ001 | 17.6 | 0.0 | 3.5 |
| CJ100 | 16.1 | 0.1 | 0 |
| CJ200 | 16.3 | 0.3 | 0 |
| CJ300 | 16.8 | 0.3 | 0 |
| CJ400 | 16.4 | 0.3 | 0 |
| CJ500 | 16.3 | 0.4 | 0 |
| CJ600 | 13.5 | 6.5 | 0 |

INDUSTRIAL APPLICABILITY

The present inventors developed the recombinant *E. coli* strain CJ600 producing tryptophan at high concentration from the *E. coli* producing L-phenylalanine without producing L-phenylalanine for a little while by releasing tryptophan auxoprotphy and mutating or inactivating genes. Particularly, the recombinant *E. coli* strain CJ600 (KCCM 10812P) was prepared from the mutant *E. coli* KFCC 10066 having L-phenylalanine productivity by releasing tryptophan auxotrophy, inactivating pheA, trpR, mtr and tnaAB genes and mutating aroG and trpE genes on chromosome. L-tryptophan was produced at high concentration by culturing the recombinant strain above, indicating that L-tryptophan productivity was increased.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for producing a recombinant *E. coli* strain having L-tryptophan productivity prepared from a mutant *E. coli* (KFCC 10066) having L-phenylalanine productivity comprising the following steps:
    selecting for expression of tryptophan biosynthetic genes trpA-E at an expression level greater than or equal to a minimum expression level necessary for growth in a tryptophan free medium,
    inactivating pheA, trpR, mtr and tnaAB genes, and mutating aroG and trpE genes on the chromosome of said *E. coli* such that the 449$^{th}$ nucleotide of the aroG gene is substituted with thymine and the 61$^{st}$ nucleotide of the trpE gene is substituted with thymine.

2. The method of claim 1, wherein the recombinant *E. coli* strain is *Escherichia coli* CJ600 (KCCM 10812P).

* * * * *